United States Patent [19]

Swain

[11] Patent Number: 4,658,807
[45] Date of Patent: Apr. 21, 1987

[54] METHOD FOR SUPPORTING AND POSITIONING THE HUMAN ANATOMY

[75] Inventor: Stephen C. Swain, Rowayton, Conn.

[73] Assignee: International Positioning Systems, Ltd., New York, N.Y.

[21] Appl. No.: 436,649

[22] Filed: Oct. 25, 1982

[51] Int. Cl.[4] ........................ A61F 13/00; A61F 5/02
[52] U.S. Cl. ...................................... 128/78; 128/134
[58] Field of Search ............... 128/75, 78, 89 B, 89 R, 128/68, 132–135; D24/64; 4/480, 572; 5/443, 444; 297/452, 460, 464, 284

[56] References Cited

U.S. PATENT DOCUMENTS

| 458,804 | 9/1891 | Ellis | 128/89 R |
|---|---|---|---|
| 1,074,615 | 10/1913 | Folmer | 297/464 |
| 1,100,430 | 6/1914 | Haas | 128/78 |
| 2,541,487 | 2/1951 | Triplett | D24/64 |
| 3,094,984 | 6/1963 | Jewett | 128/78 |
| 3,609,778 | 10/1971 | Zeiner | 5/444 |
| 3,620,211 | 11/1971 | Goodell | 128/89 R |
| 3,942,522 | 3/1976 | Wilson | 128/89 |
| 3,945,376 | 3/1976 | Kuehnegger | 128/78 |
| 4,202,327 | 5/1980 | Glancy | 128/78 |
| 4,234,228 | 11/1980 | Flamm | 297/464 |
| 4,245,627 | 1/1981 | Mignard | 128/75 |
| 4,285,336 | 8/1981 | Oebser et al. | 128/75 |
| 4,484,778 | 11/1984 | Cousins et al. | 297/460 |

Primary Examiner—Richard J. Apley
Assistant Examiner—S. R. Crow
Attorney, Agent, or Firm—Richard J. Birch

[57] ABSTRACT

A method for fitting to an individual and supporting and positioning the individual's anatomy. A plurality of independently adjustable support modules adapted to support a specific portion of an individual's anatomy in three dimensions are clamped to a chassis in order to position the support module in space. The support module can be fitted to the individual's anatomy either before or after clamping of the support module to the chassis. Thereafter, the clamped support module is loosened on the chassis to reposition the support module in space through rotational and/or translational movement in at least one plane with respect to the chassis in order to produce desired changes in positioning of the specific portion of the individual's anatomy. Once the position has been attained, the support module is re-clamped to the chassis to maintain the support module in its new spacial position. Each support module has a relatively deformable portion that can be bent to fit the support module to the individual's anatomy. Alternatively, the support module can have at least two support portions that are separated by a yieldable and resilient portion.

17 Claims, 11 Drawing Figures

METHOD FOR SUPPORTING AND POSITIONING THE HUMAN ANATOMY

BACKGROUND OF THE INVENTION

This invention relates generally to the field of support and positioning devices for the human body. Specifically, the invention relates to a positioning and posture control method and apparatus utilizing a system of body support modules that can be quickly and accurately shaped or reshaped to conform to the anatomy of the individual or by virtue of flexible and resilient members will shape to conform to the anatomy in response to the pressure exerted by the particular user.

Body support and positioning devices are needed in a variety of applications for positioning for maintenance of proper posture while the user performs a variety of tasks. These devices find application for persons with normal as well as abnormal anatomies. For example, the device of the present invention can be employed to position doctors and dentists and others who must work in a non-upright position, patients during surgery as well as during pre-and-post operative periods; racing car drivers, armored vehicle drivers, fighter pilots and others who are subject to high "g" forces and/or vibrations, mechanics on creepers, assembly line workers and the like.

In its deformable version, the invention finds particular applicability for custom fitting physically handicapped and developmentally disabled persons. Special wheelchairs designed to provide long term sitting comfort for trauma victims or amputees are well known in the prior art. Additionally, braces designed to aid the handicapped in their ability to stand or walk or provide orthopedic correction are also well known in the art. Representative examples of such braces and other supports are found in the following U.S. Pat. Nos.: 1,316,915; 1,935,859; 2,973,030; 3,094,984; 3,288,525; 3,605,731; 3,697,133; 3,724,144; 3,771,513; 3,938,509; 3,945,376; 4,080,962; 4,245,627 and 4,300,249.

In recent years another group of physically impaired individuals, the neurologically disabled, has created through their special needs, even more challenging requirements in the design of wheelchairs and other supporting devices. Neuromuscular disabilities stem from injury, disease or developmental disorder of the brain or central nervous system. The more severely involved lack the intelligence, balance or muscle tone to stand or even sit up properly. Over the years the lack of proper equipment and provisions for positioning these individuals has allowed them to physically develop abnormally resulting in gross deformities of their anatomies and life threatening misalignment of their vital organs. These individuals require a wheelchair with significant external support in the form of a sitting brace that controls posture through proper positioning.

The concept of "positioning" as a form of therapy has emerged as a significant means to control deformity, provide opportunity for cognitive growth and align the vital organs while feeding, during therapy or at rest. Equally important is the understanding that proper positioning can break up primitive reflex patterns and help control tonal asymmetry and contractures which are so destructive to normal physical and mental development.

Prior art chairs and wheelchairs were not intended to externally support and position the disabled and conform to the asymmetry characteristics of the deformed anatomy. Various brace designs were intended only for ambulatory patients. The state of the art is to strap the patient into standard wheelchairs that have been adapted by the addition of bolsters and cushions generally made in the carpentry shop of the hospital. Commercial sources for custom positioning inserts are nearly non-existent for a number of reasons. The first is coping with all the different variations of deformities requires an extremely adaptable and adjustable chair that is very expensive to manufacture. A second reason is a medical equipment supplier does not have enough time to go through the long and arduous fitting of each multi-adjustable positioner. Lastly, the harsh institutional environment quickly rusts the frame and breaks down the upholstery to shorten the useful life of the unit to a point that it is not economically feasible.

Therefore, it is the purpose of the present invention to provide a method and apparatus for supporting and positioning the disabled in an inexpensive system that can accommodate their various anatomical deformities, be fitted to the individual quickly and accurately and be constructed of materials tolerant of the harsh institutional environment.

In another version of this invention, it is envisioned that a number of different people may need to be positioned in the same device making custom fitting to each individual impractical. In this case, the positioning device flexes in response to pressure exerted by the shape and weight of the individual. Control of posture and position is effected by the "spring rate" or control of the amount of flexibility of the deformable elements as they yield under the weight and position of the individual.

SUMMARY OF THE INVENTION

In studying the anatomy, especially in the sitting posture, specific areas for external support can be identified. Grasping an individual under the armpits grasps hold of the rib cage. Grasping someone around the waist grasps no skeletal segment since it is lower than the ribs and higher than the pelvis. Therapists can show, by use of their hands, how they would grasp the individual to hold him siting up straight and in a position that breaks up primitive reflex patterns. This invention utilizes a series of modules shaped to conform to the specific support area in the form of anatomically engineered "hands" that mimic the instructions given by the therapists hands. These support modules are adjustably mounted to a "spine" that has been shaped to conform to the shape of the backbone of the individual. The spine with support modules are adjustably mounted to a seat plane so that back angle and seat depth are adjustable. The seat plane mounts the leg rest or in the case of the severely involved, mounts a segmented seat/leg rest assembly for balancing the lower torso with the upper torso in the case of scoliosis and consequential rib cage rotation. The support modules are designed to conform to the normal anatomy and are adjustable to conform to the abnormal anatomy.

In one embodiment, the support modules are made from a malleable metal that can be bent or deformed to match the deformity of the skeletal area it is intended to support. The modules have also been pre-weakened along certain axis so that when pressure is applied with a bending tool the module bends along bend lines that relate to the human anatomy. The malleable metal is weak enough that it can be deformed by the leverage of a large bending tool along the desired bending lines yet is strong enough to resist bending under the weight or movement of the client. Further, the metal can be bent over and over again without significant hardening or weakening, allowing not only the accuracy of the first fitting sessions but subsequent refitting as the individual grows or improves over time. A selection of various shaped interchangeable support modules each designed to satisfy specific support needs are available at the discretion of the medical staff.

Finally, to solve the state of the art upholstery inadequacies, the anatomically engineered metal shapes with a plurality of pre-weakened or relatively deformable bend axes are invested into a mold and foamed all around with a soft urethane and a hard surface skin to provide a seamless waterproof chemically resistant and strong durable yet soft shape for contact with the body.

It is, therefore, a general object of this invention to provide an improved method and apparatus for positioning and supporting the human body.

It is a specific object of this invention to use a series of interchangeable support modules that are anatomically engineered to relate and conform to specific areas of the anatomy for the support of the individual.

It is a further specific object that the interchangeable support modules can be selected with the cooperation of the medical staff and assembled and fitted on cite literally around the patient and then shaped and bent to create an external skeleton that is deformed through the fitting process to conform to the deformed internal skeleton of the patient.

It is a further object of the invention that the spine and the support modules are preweakened along certain anatomically related areas so that the direction of bending is predetermined and controlled to relate to the anatomy.

It is a feature of the invention that the material comprising the frame of the spine or support module is malleable with tools but not yielding under the weight or stress of the patient and that it can be rebent many times without failure.

It is a further feature that in the case of institutional use, the upholstery be soft yet durable, seamless and waterproof and the entire insert be removable from the standard wheelchair frame for separate cleaning.

It is still another object of the invention that in the case of a positioning device intended for use by a number of different individuals where custom fitting is not practical that the support modules flex about the certain anatomically related areas so the direction of flexing is predetermined and controlled to relate to the anatomy.

These and other objects and features of the invention will more fully appear from the following description and with reference to the following drawings in which.

DETAILED DESCRIPTION OF THE INVENTION

Figure 1:
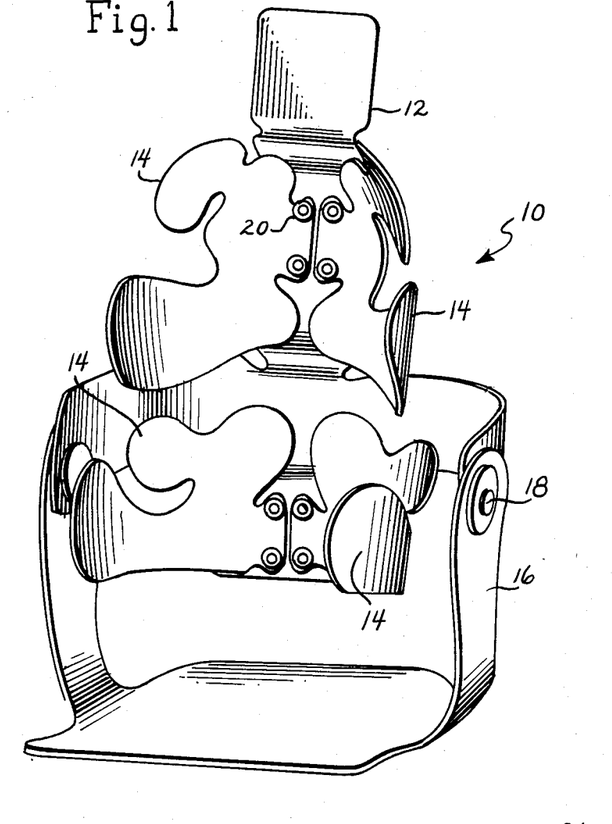
FIG. 1 is a view in perspective of the support and positioning apparatus of the present invention showing the apparatus attached to a seat pan.

Turning now to the drawings and particularly to FIG. 1, there is shown a support and positioning apparatus constructed in accordance with the present invention and indicated generally by the reference numeral 10. The support and positioning device 10 comprises a chassis 12 and a plurality of support modules 14 that have been pre-bent to generally conform to a normal anatomy. The chassis 12 is adjustably mounted with respect to a seat pan 16 by means of mounting elements 18. The adjustable mounting of the chassis provides for controlling the seatback depth and the chasis angle as it relates to the seat pan 16. The individual support modules 14 are adjustably secured with respect to the chassis 12 by means of fasteners 20 as will be described below.

Figure 2:
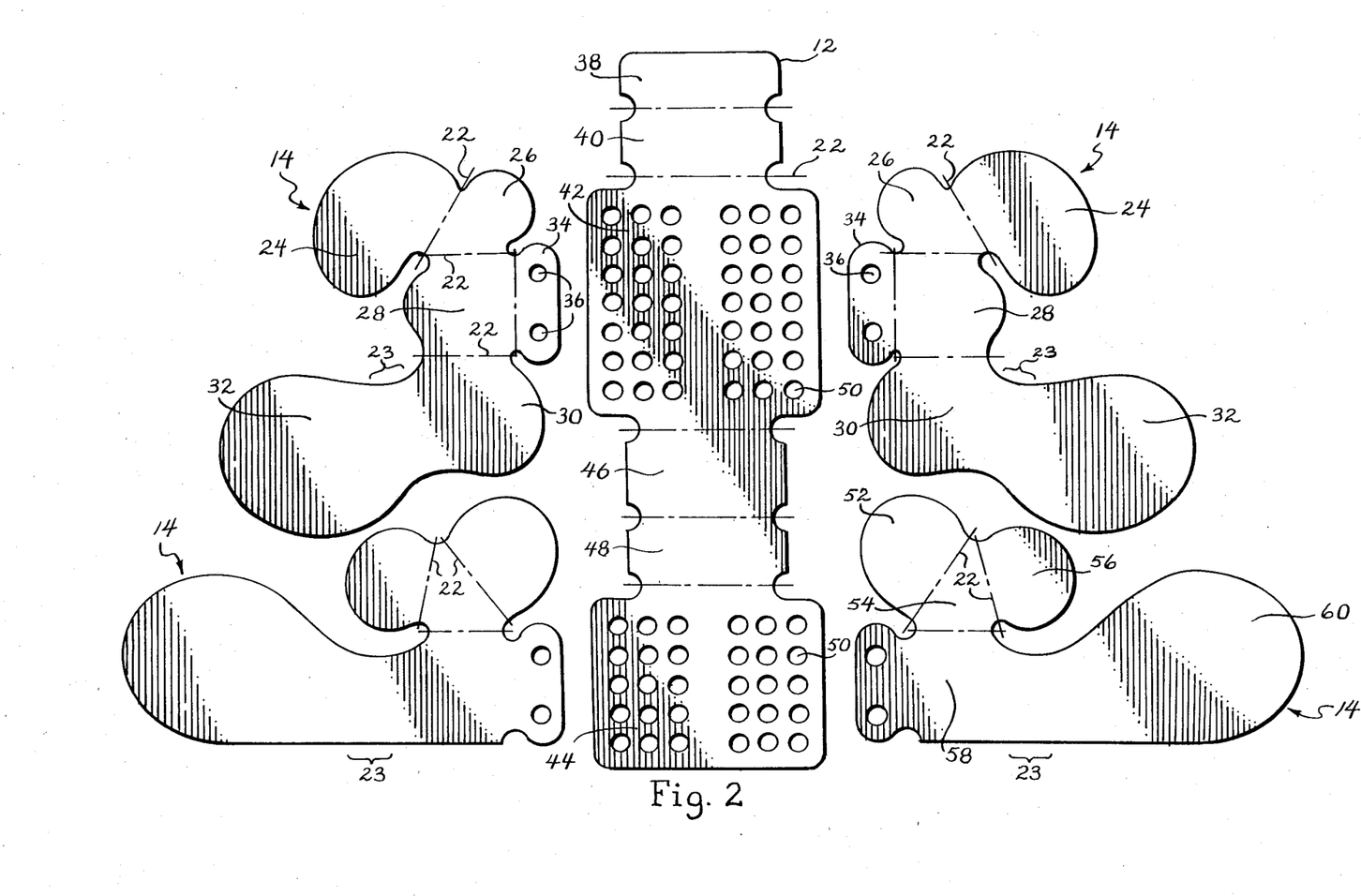
FIG. 2 is a plan view of the support modules and chassis of FIG. 1 in planar form before bending the modules and chassis about predetermined bending axes to conform the support modules and chassis to the anatomy of an invidivual.

Referring now to FIG. 2, the chassis 12 and individual support modules 14 are shown in plan view before the modules are bent along predetermined bending axes 22. The predetermined bending axes 22 are selected so that the axes relate to the human anatomy after the individual support modules 14 have been mounted on chassis 12. The predetermined bending axes 22 control the direction of bending and, therefore, the shape of the individual support modules in order to conform the modules to the normal human anatomy. Subsequent "fine tuning" by bending can then be employed in the field to custom fit a particular support and positioning device to a specific individual anatomy.

The controlled bending of the support modules about the bending axes 22 is accomplished by producing a zone or region of "relative deformability" or preweakened area in each support module. The predetermined bending axes 22 lie within the preweakened or relatively deformable portion 23.

Looking specifically at the upper right hand support module 14 in FIG. 2, it can be seen that the support module has a plurality of shaped support portions that relate to specific areas of the anatomy. This upper torso support module has a scapula contact portion 24, an upper thoracic contact portion 26, a middle thoracic contact portion 28, and a lower thoracic contact portion 30 having a lateral support portion 32 which generally contacts and supports the rib cage through the general region of the latissumus dorsi muscle group. Each one of the body contact support portions is separated from the adjacent support portion by a bending axis 22 that lies within a relatively deformable or preweakened zone 23. For purposes of clarity, the bending axis 22 has been omitted from the zone of preweakening between the lower thoracic contact portion 30 and the lateral support portion 32. However, it will be appreciated that each bending axis 22 lies within and is associated with a corresponding zone or portion of relative deformability.

The term "relative deformability" as used herein means that the area or zone 23 within which lies bending axis 22 will more readily deform under pressure than the two adjacent body contact support portions. The relative deformability of this zone can be achieved in a variety of ways. In FIG. 2, the support module is decreased in width, i.e. notched, to define each zone of relative deformability. The amount of width reduction can be varied to provide sequential bending so that bending about one predetermined bending axis will not offset another.

The support modules 14 are adjustably secured to the chassis 12 by means of the previously mentioned mounting elements 20 that extend through apertures 36. However, before mounting the support modules 14 to the chassis, the chassis 12 is bent about one or more of the bending axes 22 as shown in FIG. 2. These bending axes also lie in relatively deformable portions formed by the reduced width areas in the chassis.

The chassis 12 has a head contact portion 38, a head contact portion angle control 40, an upper torso support module mounting portion 42, a lower torso support module mounting portion 44 and lower torso portion angle controls 46 and 48.

Each lower torso support module 14 has a lumbar contact portion 52, a sacro lumbar contact portion 54, an illium contact portion 56, a sacrum contact portion 58 having a lateral support portion 60 which contact and aligns the general hip region. Each one of these contact portions is separated from the adjacent portion by a zone 23 of relative deformability within which lies the previously mentioned predetermined bending axis 22.

Both the upper and lower torso support modules 14 are adjustably mounted to the chassis 12 by means of fasteners 20 that extend through corresponding apertures 36 in the support modules. The chassis 12 has a plurality of corresponding apertures 50 that provide a variety of positions for mounting each of the support modules with respect to the chassis. Preferably, the chassis apertures 50 are larger than the support module aperture 36 to provide some degree of adjustability with respect to the mounting of the support module 14 on chassis 12. In this situation, the fasteners 20 function as clamping devices.

The relatively deformable portions 23 of the support modules 14 shown in FIG. 2 are achieved by notching or otherwise reducing the width of the support module. As mentioned above, the relatively deformable portion of the support module can be produced in other ways.

Figure 3:
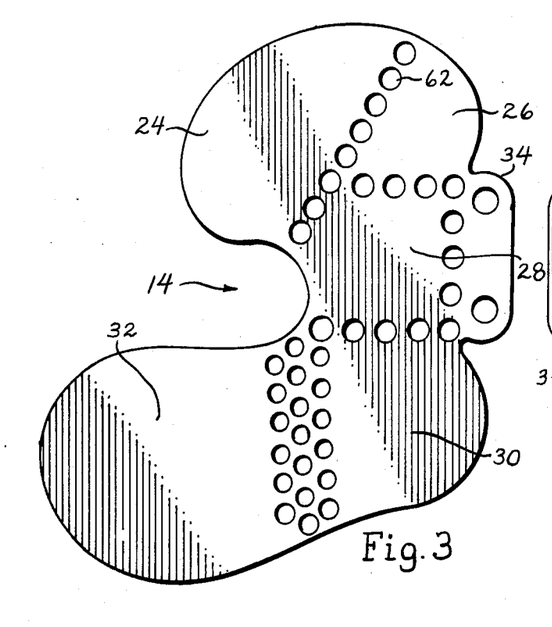
FIG. 3 is a plan view of another version of the support module in which each predetermined bending axis is created by a series of apertures.

For example, the support module 14 shown in FIG. 3 utilizes a plurality of holes 62 to define each bending axis and the portion of relative deformability. The holes 62 define bending axes that correspond to the bending axes 22 shown in FIG. 2. This can be seen by directly comparing the support module of FIG. 3 with the upper left hand support module shown in FIG. 2. It should be noted that the broader zone of relative deformability between the lower thoracic contact portion 30 and the lateral support portion 32 is created by an additional series of holes in the support module shown in FIG. 3.

Figure 4:
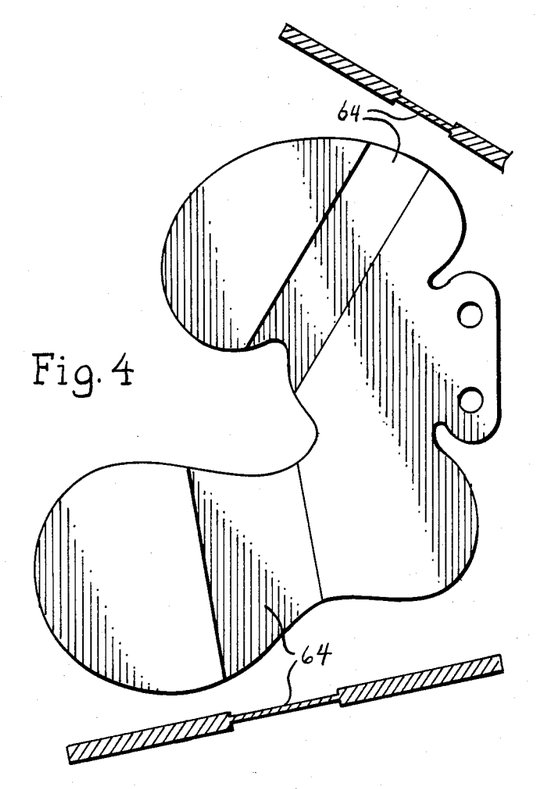
FIG. 4 is plan view of a still another version of the support module in which each predetermined bending axis is created by reducing the thickness of the module in selected areas.

FIG. 4 illustrates still another way of producing the relatively deformable portion between adjacent support portions. In FIG. 4, the area of relative deformability is produced by reducing the sheet thickness of the support module in an area identified by the reference numeral 64.

It will be appreciated that other methods can be employed to produce the relatively deformable portion in each support module and that the present invention is not limited to the reduced width, preweakening by apertures and reduced thickness techniques shown in FIGS. 2, 3 and 4, respectively. Selective hardening of the support module sheet material is feasible as are other techniques.

Figure 5:
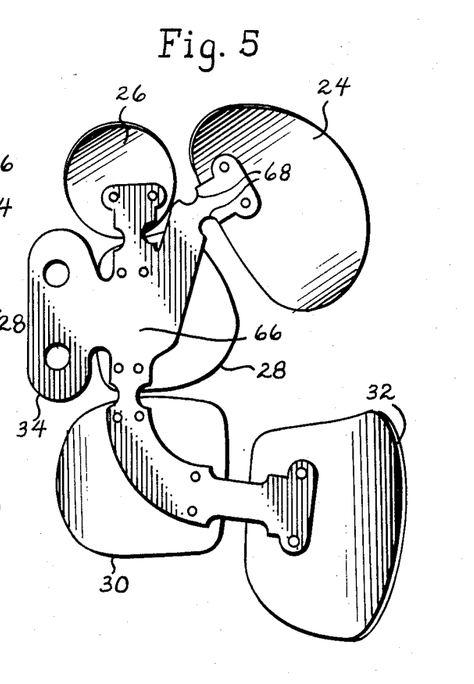
FIG. 5 is a perspective front view of a support module in which the body contact support elements are mounted to a frame with the predetermined bending axes created by notching or narrowing the width of the frame.

Turning now to FIG. 5, the support module 14 shown therein is formed from separate pieces rather than as a unitary sheet element as shown in FIG. 2. FIG. 5 illustrates the shaped support portions (reference numerals 24-32) of the upper torso support module attached to a deformable frame 66 having corresponding predetermined bending axes formed by reduced width portions resulting from notches 68.

Figure 6:
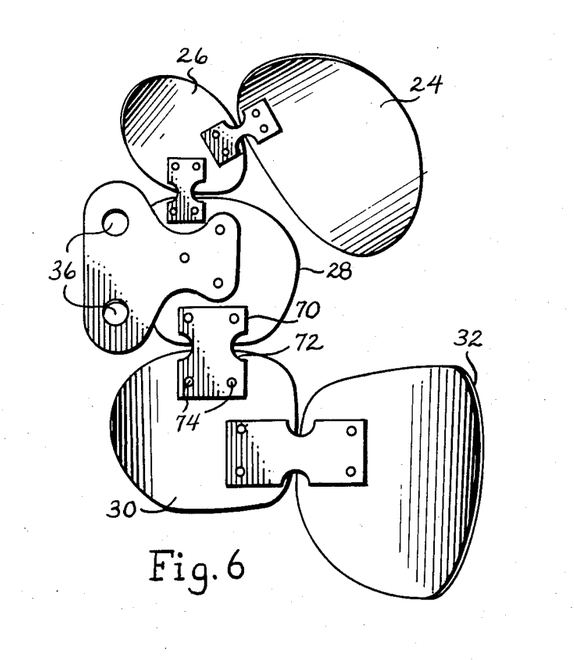
FIG. 6 is a perspective front view of a support module in which the body contact support elements are mounted to each other by a series of independent frames each having a predetermined bending axis that is created by notching or narrowing the width of the frame.

The structure illustrated in FIG. 6 is similar to that shown in FIG. 5 with the shaped support portions of the upper torso support module 14 separately formed, but in contrast to FIG. 5, the support portions are attached to each other by mounting members 70 each having a relatively deformable portion defined by the reduced width area resulting from notches 72. Depending upon the specific embodiment, the mounting members 70 are either nearly permanently deformable (in the case of a custom fitted support and positioning device) or yieldable and resilient (as in the case of positioning or support devices used by a number of individuals). The predetermined bending axis or flexing axis (in the case of the yieldable and resilient member) is determined by the relative angle of mounting of the member 70 and notches 72 with respect to each individual support portion. Mounting of the member 70 to the support portions can be accomplished by using standard mounting techniques such as, rivets 74.

Figure 7:
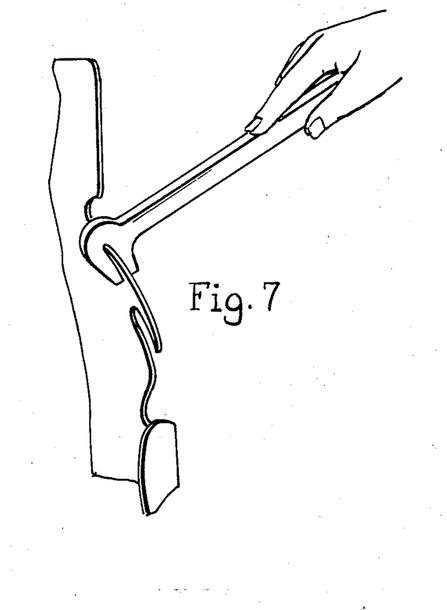
FIG. 7 is a perspective view showing the bending technique employed to fit individual support modules to a particular anatomy.

Referring back to FIG. 1, it can be seen that the support and positioning apparatus 10 has been mounted to the seat pan 16 and the chassis 12 and support modules 14 have been pre-bent to generally conform to the normal anatomy. In the case of the developmentally disabled or even a race car driver, it is desirable to alter or custom fit the support and positioning device 10 to exactly conform to the position or posture requirements of the individual and his task. Custom fitting or adjustment of the support and positioning apparatus 10 is accomplished by bending the individual support portions of each support module about the bending axes 22. The bending technique is illustrated in FIG. 7 in which a bending tool applies pressure through leverage to the selected support portion requiring adjustment. As pressure is applied to the support portion, the "pre-weakened" or relatively deformable area of the adjacent predetermined bending axis will deform and bend prior to any distortion to the support portion.

It has already been mentioned that the predetermined bending axis is related to the anatomy when the support module is mounted on chassis 12. FIGS. 8 through 11 diagrammatically illustrate the relationship of these axes to the normal as well as the abnormal anatomy.

Figure 8:
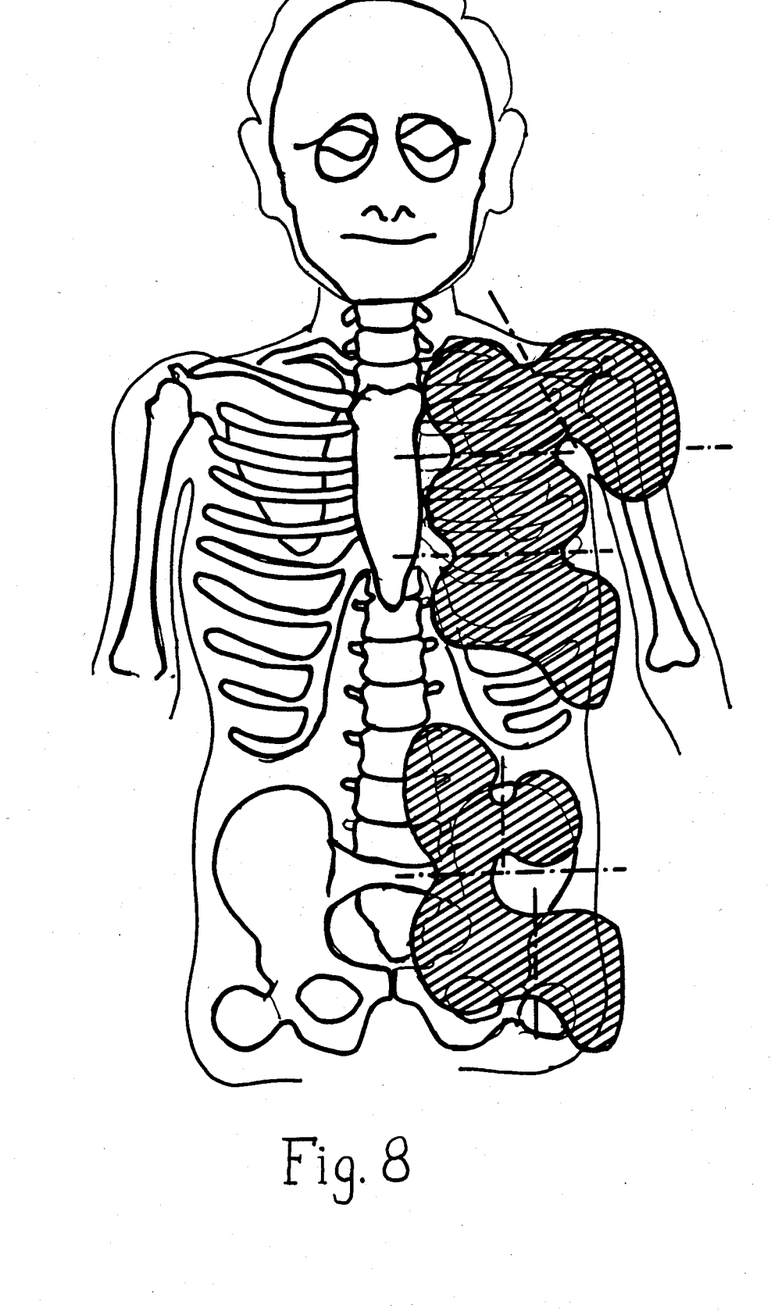
FIG. 8 is a front view of a normal anatomy illustrating the shape of the support modules, the location of the predetermined bending axes and their relationship to the skeleton.
Figure 9:
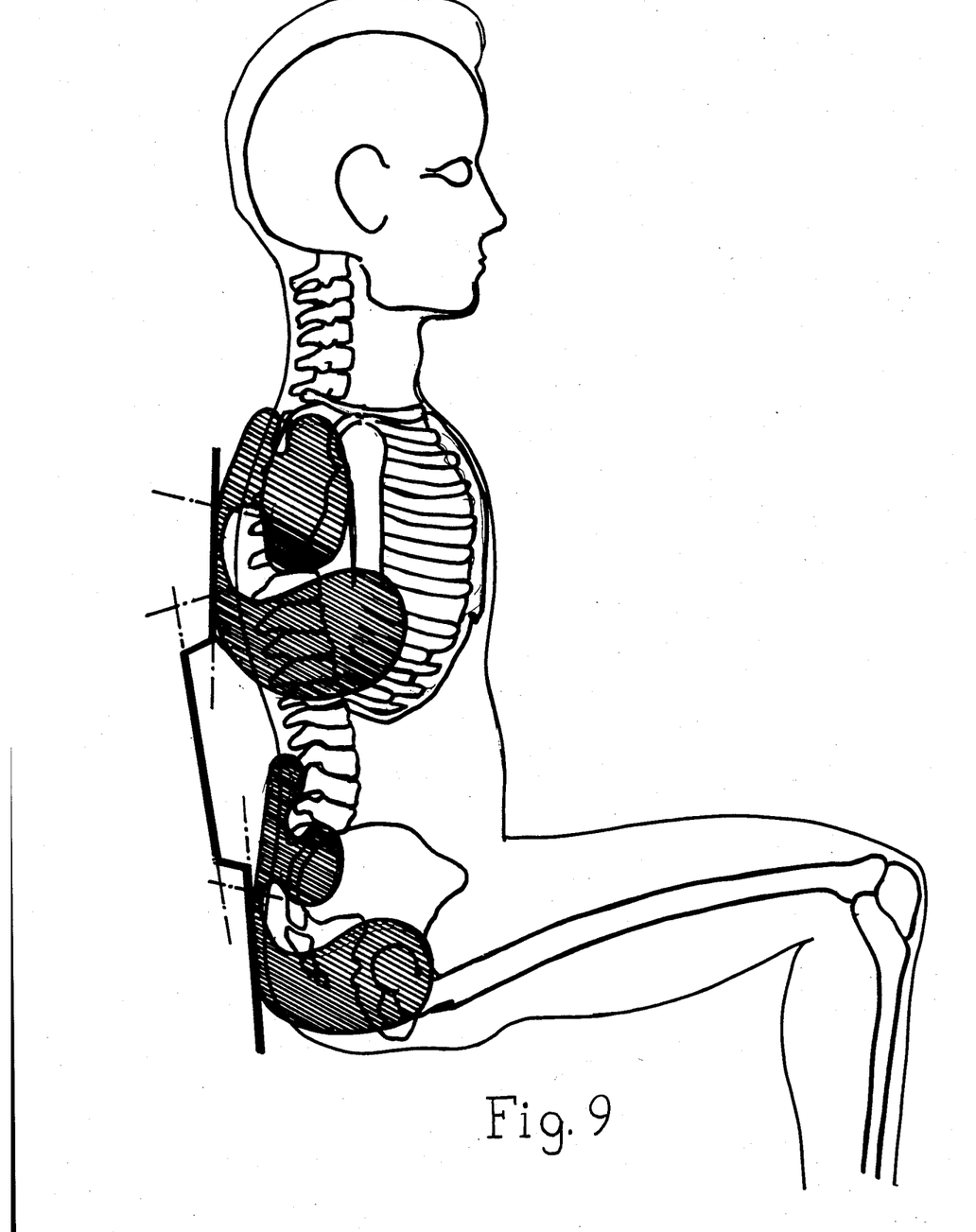
FIG. 9 is a side view of a normal anatomy illustrating the shape of the support modules and chassis, the location of predetermined bending axes and their relationship to the skeleton.

The illustration of FIG. 8 depicts the numerous bending axes as they relate to the human anatomy. The lumbar contact support portion 52 of the lower torso support module is used to maintain the important "S" curve that aligns the lower vertebrae correctly in the lumbar region. The illium contact portion 56 also helps to shape the lumbar by contacting and tilting the pelvis. The upper torso support modules (shown overlayed with the anatomy) provide support and conform to the roundness of the upper back. This is accomplished by means of the bending that occurs about the two predetermined bending axes between the upper, middle and lower thoracic contact portions as shown in FIGS. 9–11.

Figure 10:
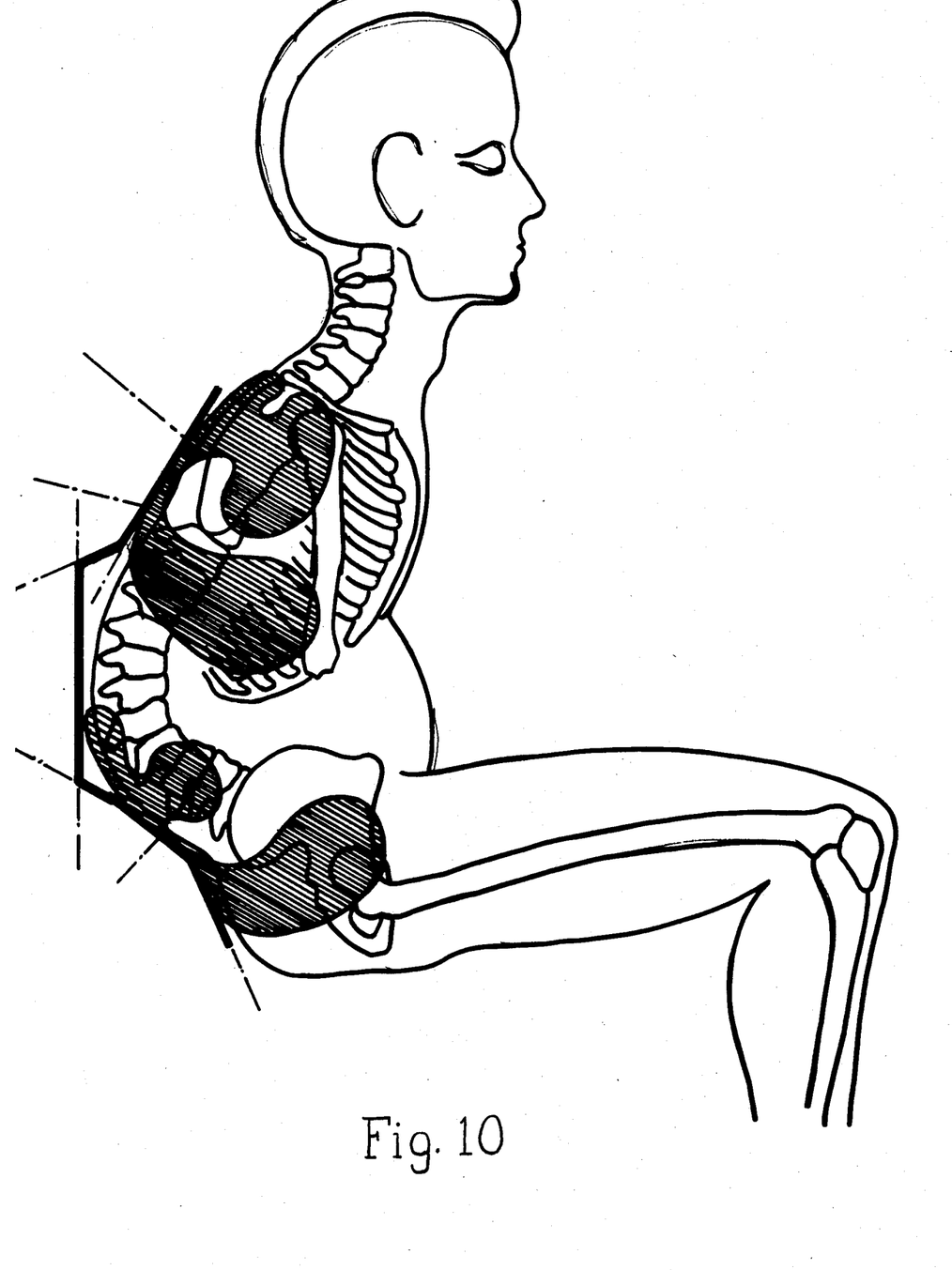
FIG. 10 is a side view of an abnormal anatomy illustrating the altered shape of the support modules and chassis after fitting to conform to the abnormal anatomy; and, FIG. 11 is a front view of the abnormal anatomy illustrating the use of asymmetric support modules and an angled seat pan for positioning and balancing the abnormal anatomy.
Figure 11:
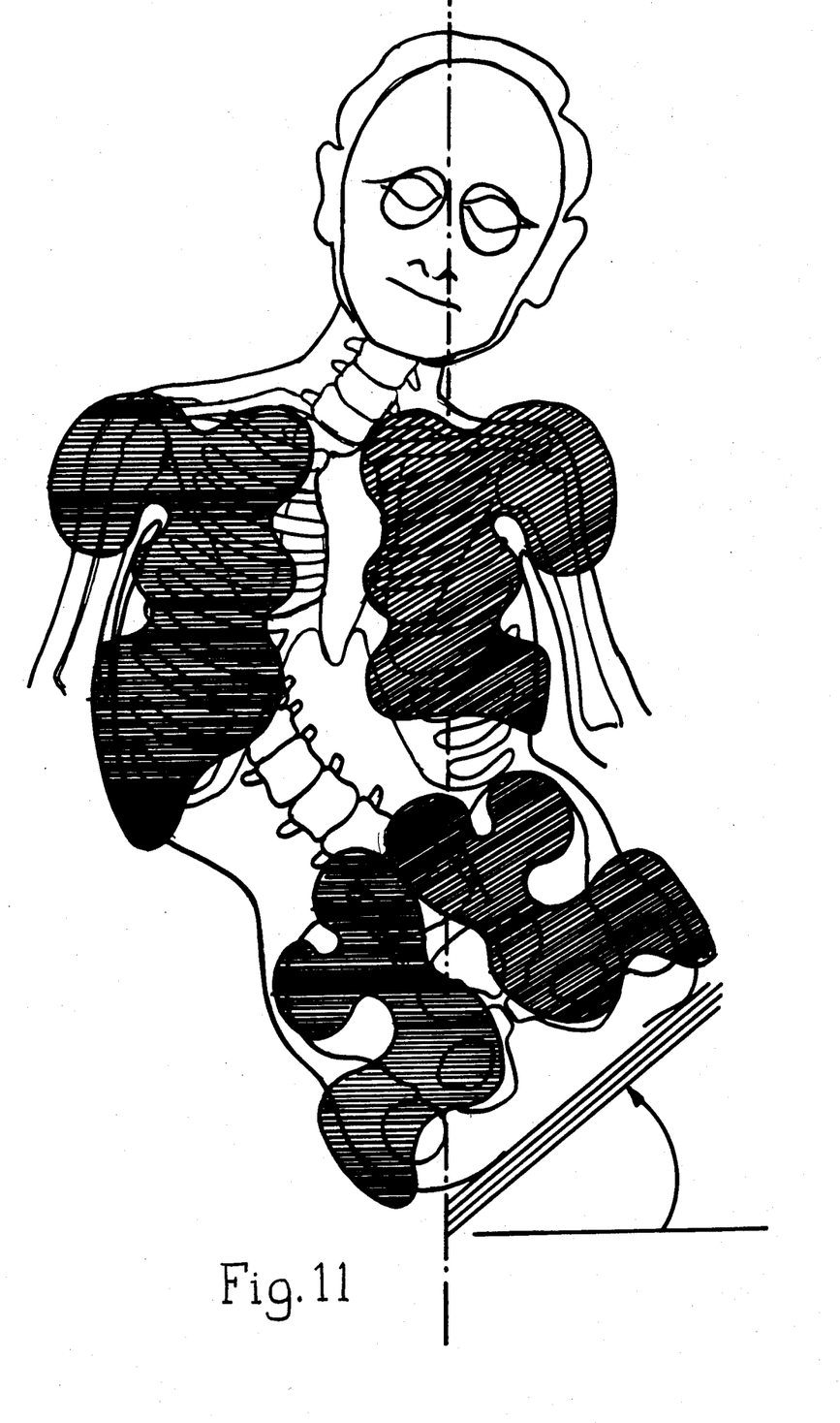

FIGS. 10 and 11 illustrate the use of the support and positioning apparatus 10 for deformed anatomies. FIG. 11 shows the choice of asymmetric support modules and the bending or tilting of the seat pan plane in order to balance the skeleton.

Having described a preferred embodiment of my invention, it will be apparent to those skilled in the art that numerous modifications can be made therein without departing from the scope of the invention as defined in the following claims. For example, the chassis and support modules shown in FIGS. 1–4 can be constructed as a single unitary element rather than as a separate chassis and individual support modules mounted thereon. Furthermore, suitable upholstery, such as, invested foam can be placed over the structural elements. In this case, the bending must be done "blind". However, the predetermined bending axes 22 control the bending even though the fitter cannot see the location of the bending axes.

What I claim and desire to secure by Letters Patent of the United States is:

1. A method for fitting to an individual an apparatus for supporting and positioning the individual's anatomy, said method comprising the steps of:
   (1) selecting a support module adapted to support a specific portion of an individual's anatomy in three dimensions, said support module having at least two support portions that are separated by a relatively deformable, shape retainable portion;
   (2) fitting the support module to conform to the specific portion of the individual's anatomy by bending the relatively deformable, shape retainable portion of the support module;
   (3) positioning the fitted support module in space by clamping the support module to a chassis with the spacial positioning of the support module being related to the specific portion of the individual's anatomy when the support module is used to position said anatomy portion; and, thereafter
   (4) loosening the clamped support module on the chassis to reposition the support module in space through rotational and/or translational movement in at least one plane with respect to said chassis in order to produce desired changes in positioning of the specific portion of the individual's anatomy, and reclamping the support module to the chassis to maintain the support module in its new spacial position.

2. A method for fitting to an individual an apparatus for supporting and positioning the individual's anatomy, said method comprising the steps of:
   (1) securing at least one support module to a chassis by clamping the support module to the chassis, said support module being adapted to support a specific portion of an individual's anatomy in three dimensions and having at least two support portions that are separated by a relatively deformable, shape retainable portion;
   (2) fitting the support module to conform to the specific portion of the individual's anatomy by bending the relatively deformable, shape retainable portion of the support module;
   (3) positioning the fitted support module in space by loosening and then reclamping the support module to the chassis with the specific positioning of the support module being related to the specific portion of the individual's anatomy when the support module is used to position said anatomy portion; and, thereafter
   (4) loosening the clamped support module on the chassis to reposition the support module in space through rotational and/or translational movement in at least one plane with respect to said chassis in order to produce desired changes in position of the specific portion of the individual's anatomy, and reclamping the support module to the chassis to maintain the support module in its new spacial position.

3. A method for fitting to an individual an apparatus for supporting and positioning the individual's anatomy, said method comprising the steps of:
   (1) selecting a plurality of independently positionable support modules each adapted to support a specific portion of the individual's anatomy in three dimensions, said support modules each having at least two support portions that are separated by a relatively deformable, shape retainable portion;
   (2) fitting the support modules to conform to the corresponding specific portion of the individual's anatomy by bending the relatively deformable, shape retainable portion of each support module;
   (3) independently positioning the fitted support modules in space by clamping the support modules to a chassis with the spacial positioning of the support modules being related to the specific portion of the corresponding individual's anatomy when the support module is used to position said anatomy portion; and, thereafter
   (4) loosening the clamped support modules on the chassis to reposition the support modules in space through rotational and/or translational movement in at least one plane with respect to said chassis in order to produce desired changes in positioning of the corresponding specific portion of the individual's anatomy, and reclamping the support modules to the chassis to maintain each support module in its new spacial position.

4. A method for fitting to an individual an apparatus for supporting and positioning the individual's anatomy, said method comprising the steps of:
   (1) securing a plurality of independently positionable support modules to a chassis by clamping the support modules to the chassis, said support modules each being adapted to support a specific portion of an individual's anatomy in three dimensions and said support modules each having at least two support portions that are separated by a relatively deformable, shape retainable portion;

(2) fitting the support modules to conform to the corresponding specific portion of the individual's anatomy by bending the relatively deformable, shape retainable portion of the support module;

(3) independently positioning the fitted support modules in space by loosening and then reclamping the support modules to the chassis with the specific positioning of the support modules being related to the corresponding specific portion of the individual's anatomy when the support module is used to position said anatomy portion; and, thereafter (4) loosening the clamped support modules on the chassis to reposition the support modules in space through rotational and/or translational movement in at least one plane with respect to said chassis in order to produce desired changes in position of the corresponding specific portion of the individual's anatomy, and reclamping the support modules to the chassis to maintain each support module in its new spacial position.

5. A method for fitting to an individual an apparatus for supporting and positioning the individual's anatomy, said method comprising the steps of:

(1) selecting a support module adapted to support a specific portion of an individual's anatomy in three dimensions, said support module having at least two support portions that are separated by a relatively deformable, shape retainable portion;

(2) fitting the support module to conform to the specific portion of the individual's anatomy by bending the relatively deformable, shape retainable portion of the support module;

(3) loosely clamping the fitted support module to a first chassis;

(4) clamping the first chassis with the loosely clamped fitted support module thereon to a second chassis; and thereafter, (5) positioning the fitted support module in space through rotational and/or translational movement of the support module with respect to the chassis in a plane in order to produce the desired positioning of the specific portion of the individual's anatomy, and then tightly clamping the support module to the first chassis to maintain the support module in its new spacial position.

6. A method for fitting to an individual an apparatus for supporting and positioning the individual's anatomy, said method comprising the steps of:

(1) selecting a support module adapted to support a specific portion of an individual's anatomy in three dimensions, said support module having at least two support portions that are separated by a relatively deformable, shape retainable portion;

(2) fitting the support module to conform to the specific portion of the individual's anatomy by bending the relatively deformable, shape retainable portion of the support module;

(3) clamping the fitted support module to a first chassis;

(4) loosely clamping the first chassis with the clamped fitted support module thereon to a second chassis; and, thereafter (5) positioning the fitted support module in space through rotational and/or translational movement of the first chassis in a plane with respect to the second chassis in order to produce the desired positioning of the specific portion of the individual's anatomy, and then tightly clamping the first chassis to the second chassis to maintain the support module in its spacial position.

7. A method for fitting to an individual an apparatus for supporting and positioning the individual's anatomy, said method comprising the steps of:

(1) selecting a support module adapted to support a specific portion of an individual's anatomy in three dimensions, said support module having at least two support portions that are separated by a relatively deformable, shape retainable portion;

(2) fitting the support module to conform to the specific portion of the individual's anatomy by bending the relatively, shape retainable deformable portion of the support module;

(3) loosely clamping together the fitted support module, a first chassis and a second chassis with said fitted support module being clamped to the first chassis and the first chassis being clamped to the second chassis; and, thereafter (4) positioning the support module in space through rotational and/or translational movement of the support module and first chassis in at least one plane in order to produce desired positioning of the specific portion of the individual's anatomy, and then tightly clamping the support module to the first chassis and the first chassis to the second chassis in order to maintain the support module in this spacial position.

8. A method for fitting to an individual an apparatus for supporting and positioning the individual's anatomy, said method comprising the steps of:

(1) selecting a support module adapted to support a specific portion of an individual's anatomy in three dimensions, said support module having at least two support portions that are separated by a relatively deformable, shape retainable portion;

(2) fitting the support module to conform to the specific portion of the individual's anatomy by bending the relatively deformable, shape retainable portion of the support module;

(3) mounting the fitted support module to a chassis by loosely clamping the fitted support module to the chassis; and, thereafter (4) positioning the fitted support module in space through rotational and/or translational movement of the fitted support module in at least one plane with respect to said chassis in order to produce the desired positioning of the specific portion of the individual's anatomy, and then tightly clamping the fitted support module to the chassis to maintain the fitted support module in this spacial position.

9. A method for fitting to an indivdual an apparatus for supporting and positioning the individual's anatomy, said method comprising the steps of:

(1) securing a support module to a chassis by tightly clamping the support module to the chassis, said support module being adapted to support a specific portion of an individual's anatomy in three dimensions and having at least two support portions that are separated by a relatively deformable, shape retainable portion;

(2) fitting the support module to conform to the specific portion of the individual's anatomy by bending the relatively deformable, shape retainable portion of the support module;

(3) loosening the clamped fitted support module; and, thereafter (4) positioning the fitted support module in space through rotational and/or translational movement of the fitted support module in at least one plane with respect to said chassis in order to produce the desired positioning of the specific portion of the individual's anatomy, and then tightly reclamping the fitted support module to the chassis to maintain the fitted support module in this spacial position.

10. A method for fitting to an individual an apparatus for supporting and positioning the individual's anatomy, said method comprising the steps of:

(1) selecting a plurality of independently positionable support modules each adapted to support a specific portion of the individual's anatomy in three dimensions, said support modules each having at least two support portions that are separated by a relatively deformable, shape retainable portion;

(2) fitting the support modules to conform to the corresponding specific portion of the individual's anatomy by bending the relatively deformable, shape retainable portion of each support module;

(3) mounting the fitted support modules to a chassis by loosely clamping the fitted support modules to the chassis; and, thereafter (4) independently positioning the fitted support modules in space through rotational and/or translational movement of the fitted support modules in at least one plane with respect to said chassis in order to produce the desired positioning of the corresponding specific portion of the individual's anatomy, and then tightly clamping the fitted support modules to the chassis to maintain each fitted support module in its spacial position.

11. A method for fitting to an individual an apparatus for supporting and positioning the individual's anatomy, said method comprising the steps of:

(1) securing a plurality of independently positionable support modules to a chassis by tightly clamping the support modules to the chassis, said support modules each being adapted to support a specific portion of an individual's anatomy in three dimensions and said support modules each having at least two support portions that are separated by a relatively deformable, shape retainable portion;

(2) fitting the support modules to conform to the corresponding specific portion of the individual's anatomy by bending the relatively deformable, shape retainable portion of the support module;

(3) loosening the clamped fitted support modules; and, thereafter (4) independently positioning the fitted support modules in space through rotational and/or translational movement of the fitted support modules in at least one plane with respect to said chassis in order to produce the desired positioning of the corresponding specific portion of the individual's anatomy, and then tightly clamping the fitted support modules to the chassis to maintain each fitted support module in its spacial position.

12. A method for fitting to an individual an apparatus for supporting and positioning the individual's anatomy, said method comprising the steps of:

(1) selecting a support module adapted to support a specific portion of an individual's anatomy in three dimensions, said support module having at least two support portions that are separated by a yieldable and resilient portion;

(2) mounting the support module to a chassis by loosely clamping the support module to the chassis; and, thereafter (3) independently positioning the support module in space through rotational and/or translational movement of the support module in at least one plane with respect to said chassis in order to produce the desired positioning of the specific portion of the individual's anatomy when said yieldable and resilient portion and said two support portions conform to the specific portion of the individual anatomy in response to pressure therefrom, and then tightly clamping the support module to the chassis to maintain the fitted support module in this spacial position.

13. A method for fitting to an individual an apparatus for supporting and positioning the individual's anatomy, said method comprising the steps of:

(1) selecting a plurality of independently positionable support modules each adapted to support a specific portion of the individual's anatomy in three dimensions, said support modules each having at least two support portions that are separated by a yieldable and resilient portion; and, thereafter (2) mounting the support modules to a chassis by loosely clamping the support modules to the chassis; and, thereafter (3) independently positioning the fitted support modules in space through rotational and/or translational movement of the fitted support modules in at least one plane with respect to said chassis in order to produce the desired positioning of the corresponding specific portion of the individual's anatomy when said yieldable and resilient portion and said two support portions conform to the specific portion of the individual's anatomy in response to pressure therefrom, and then tightly clamping the fitted support modules to the chassis to maintain each fitted support module in its spacial position.

14. A method for fitting to an individual an apparatus for supporting and positioning the individual's anatomy, said method comprising the steps of:

(1) selecting a support module adapted to support a specific portion of an individual's anatomy in three dimensions, said support module having at least two support portions that are separated by a yieldable and resilient portion;

(2) loosely clamping the support module to a first chassis;

(3) clamping the first chassis with the loosely clamped support module thereon to a second chassis; and thereafter, (4) positioning the support module in space through rotational and/or translational movement of the support module in at least one plane with respect to said first chassis in order to produce the desired positioning of the specific portion of the individual's anatomy when said yieldable and resilient portion and said two support portions conform to the specific portion of the individual anatomy in response to pressure therefrom, and then tightly clamping the support module to the first chassis to maintain the support module in this spacial position.

15. A method for fitting to an individual an apparatus for supporting and positioning the individual's anatomy, said method comprising the steps of:
  (1) selecting a support module adapted to support a specific portion of an individual's anatomy in three dimensions, said support module having at least two support portions that are separated by a yieldable and resilient portion;
  (2) clamping the support module to a first chassis;
  (3) loosely clamping the first chassis with the clamped support module thereon to a second chassis; and, thereafter
  (4) positioning the fitted support module in space through rotational and/or translational movement of the first chassis in at least one plane with respect to the second chassis in order to produce the desired positioning of the specific portion of the individual's anatomy when said yieldable and resilient portion and said two support portions conform to the specific portion of the individual anatomy in response to pressure therefrom, and then tightly clamping the first chassis to the second chassis to maintain the support module in this spacial position.

16. A method for fitting to an individual an apparatus for supporting and positioning the individual's anatomy, said method comprising the steps of:
  (1) selecting a support module adapted to support a specific portion of an individual's anatomy in three dimensions, said support module having at least two support portions that are separated by a yieldable and resilient portion;
  (2) loosely clamping together the support module, a first chassis and a second chassis with said support module being clamped to the first chassis and the first chassis being clamped to the second chassis; and, thereafter
  (3) positioning the support module in space through rotational and/or translational movement of the support module and first chassis in at least one plane in order to produce desired positioning of the specific portion of the individual's anatomy when said yieldable and resilient portion and said two support portions conform to the specific portion of the individual anatomy in response to pressure therefrom, and then tightly clamping the support module to the first chassis and the first chassis to the second chassis in order to maintain the support module in this spacial position.

17. The method of claim 6 wherein said support module is fitted to conform to the specific portion of the individual's anatomy by bending the relatively deformable portion of the support module after the support module is clamped to the first chassis.

* * * * *